(12) United States Patent
Breton et al.

(10) Patent No.: US 6,291,532 B1
(45) Date of Patent: *Sep. 18, 2001

US006291532B1

(54) USE OF N-ARYL-2-HYDROXYALKYLAMIDES FOR STIMULATING OR INDUCING HAIR GROWTH AND/OR ARRESTING HAIR LOSS

(75) Inventors: Lionel Breton, Versailles; Jean-Baptiste Galey, Aulnay-sous-Bois, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/142,473
(22) PCT Filed: Mar. 5, 1997
(86) PCT No.: PCT/FR97/00389
  § 371 Date: Dec. 7, 1998
  § 102(e) Date: Dec. 7, 1998
(87) PCT Pub. No.: WO97/32562
  PCT Pub. Date: Sep. 12, 1997

(30) Foreign Application Priority Data

Mar. 6, 1996 (FR) .................................................. 96 02828
Apr. 5, 1996 (FR) .................................................. 96 04362

(51) Int. Cl.[7] .......................... A61K 7/135; A61K 7/06; A01N 33/02; A01N 25/00
(52) U.S. Cl. .......................... 514/649; 424/62; 424/70.1; 424/70.6; 514/252; 514/649; 514/776; 514/880
(58) Field of Search .......................... 424/62, 70.1, 70.6; 514/252, 773, 272, 649, 880; 536/17.2; 544/320

(56) References Cited

U.S. PATENT DOCUMENTS 5,656,264 * 8/1997 Hanada et al. .................. 424/70.1

FOREIGN PATENT DOCUMENTS

| 0 002 892 | 7/1979 | (EP) . |
| 0 040 932 | 12/1981 | (EP) . |
| 0 098 743 | 1/1984 | (EP) . |
| 0 524 781 | 1/1993 | (EP) . |
| 0 699 430 | 3/1996 | (EP) . |
| 2278054 | * 11/1994 | (GB) . |
| 62-252711 | * 11/1987 | (JP) . |

OTHER PUBLICATIONS

Database WPI, Week 9008, Derwent Publications Ltd., London, GB; AN 90–056180, XP002017367 "Hair tonic cosmetic with good hair-growth-promoting action-contains odd-carbon fatty acids and aliphatic alcohol(s), and ortho-toluidine derivs." & JP 20 011 509, Jan. 16, 1990.

* cited by examiner

*Primary Examiner*—Thurman K. Page
*Assistant Examiner*—S. Tran
(74) *Attorney, Agent, or Firm*—Burns, Doane, Swecker & Mathis, L.L.P.

(57) ABSTRACT

Methods and compositions for induction or stimulation of hair growth and retardation of hair loss are provided. Preferably, these compounds will include a perhalogenated alkyl radical having 1 to 4 carbon atoms.

43 Claims, No Drawings

USE OF N-ARYL-2-HYDROXYALKYLAMIDES FOR STIMULATING OR INDUCING HAIR GROWTH AND/OR ARRESTING HAIR LOSS

The present invention relates to the use as active principle, in a physiologically acceptable medium, in a cosmetic composition or for the preparation of a pharmaceutical composition, of an effective amount of at least one specific compound from the family of the N-aryl-2-hydroxyalkylamides, intended to induce and/or stimulate hair growth and/or to slow down hair loss.

In man, hair growth and its renewal are mainly determined by the activity of the hair follicles. Their activity is cyclical and essentially comprises three phases, namely the anagen phase, the catagen phase and the telogen phase.

The active anagen phase or growth phase, which lasts several years and during which the hair lengthens, is succeeded by a very short and transitory catagen phase, which lasts a few weeks, and then by a resting phase, also known as the telogen phase, which lasts a few months.

At the end of the period of rest, the hairs fall out and another cycle commences. The head of hair is thus constantly renewed and at any moment, out of the approximately 150,000 hairs which a head of hair comprises, approximately 10% of them are at rest and will thus be replaced in a few months.

However, various causes can result in a significant, temporary or permanent, hair loss. Alopecia is essentially due to a disturbance of hair renewal which results, firstly, in an acceleration in the frequency of the cycles at the expense of the quality of the hair and then of its amount. A gradual thinning of the head of hair takes place by regression of the so-called "terminal" hairs at the downy stage. Areas are preferentially affected, in particular the temples or the front of the head in men, and, in women, a diffuse alopecia of the vertex is observed.

The term alopecia covers a whole family of conditions of the hair follicle having, as final consequence, partial or general permanent hair loss. In a significant number of cases, early hair loss takes place in genetically predisposed subjects and it effects men in particular. It relates more particularly to androgenetic or androgenic or even androgeno-genetic alopecia.

There has been a search for many years, in the cosmetic or pharmaceutical industry, for substances which make it possible to eliminate or reduce alopecia and in particular to induce or stimulate hair growth or to decrease hair loss.

From this viewpoint, a large number of very diverse active compounds have certainly already been provided, such as, for example, 2,4-diamino-6-piperidinopyrimidine 3-oxide or "Minoxidil", disclosed in Patents U.S. Pat. No. 4,139,619 and U.S. Pat. No. 4,596,812, or its numerous derivatives, such as those disclosed, for example, in Patent Applications EP 0,353,123, EP 0,356,271, EP 0,408,442, EP 0,522,964, EP 0,420,707, EP 0,459,890 and EP 0,519,819.

It remains generally the case that it would be advantageous and useful to be able to have available active compounds other than those already known which are potentially more active and/or less toxic.

This aim and others are achieved by the present invention which relates to the use as active principle, in a physiologically acceptable medium, in a cosmetic composition or for the preparation of a pharmaceutical composition, of an effective amount of at least one compound corresponding to the general formula (I):

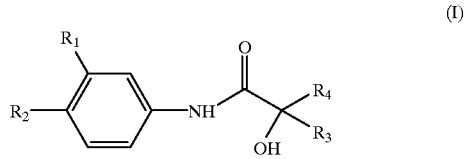

in which
$R_1$ is a cyano group, a halogen atom or an alkyl group, having from 1 to 4 carbon atoms, substituted by at least one halogen atom;
$R_2$ is a cyano group or a halogen atom;
$R_3$ is an alkyl group, having 1 or 2 carbon atoms, optionally substituted by at least one halogen atom;
$R_4$ is a hydrogen atom or an alkyl group, having from 1 to 4 carbon atoms, substituted by at least one halogen atom, or an aryl group, optionally substituted by one or more halogen atoms or by one or more hydroxyl, carboxyl, nitro, cyano, linear or branched alkyl, having 1 to 4 carbon atoms, linear or branched alkoxy, having 1 to 4 carbon atoms, linear or branched alkanoyl, having 1 to 4 carbon atoms, or perfluoroalkyl groups;
or of at least one of its isomers, of at least one of its acylated forms or alternatively of at least one of its salts;
this compound or the pharmaceutical composition being intended to induce and/or stimulate hair growth and/or to slow down hair loss.

These compounds exhibit notable activities which justify their use as active principle for inducing and/or stimulating hair growth and/or slowing down hair loss.

This is because they are excellent openers of potassium channels, the main property of Minoxidil, the only compound recognized to date as effective in the treatment of hair loss They are also excellent receptorial antagonists of androgens, androgens being responsible for a particularly widespread form of alopecia, androgen-dependent alopecia.

To the knowledge of the Applicant Company, provision has never been made in the prior art for the use of such compounds possessing mixed activity, openers of potassium channels/antiandrogens, for controlling hair loss.

According to a specific embodiment of the invention, $R_1$. can be a chlorine, bromine or fluorine atom, preferably a chlorine atom.

According to another embodiment of the invention, $R_1$, can be an alkyl group, having from 1 to 4 carbon atoms, substituted by at least one chlorine, bromine or fluorine atom. $R_1$, is preferably an alkyl group, having from 1 to 4 carbon atoms, substituted by at least one fluorine atom, more preferably $R_1$, is a perhalogenated alkyl radical, having from 1 to 4 carbon atoms, more preferably still $R_1$, is a perhalogenated methyl radical and more preferably still $R_1$, is a perfluorinated methyl radical.

When $R_2$ is a halogen atom, $R_2$ can be a chlorine, bromine or fluorine atom; $R_2$ is preferably a chlorine atom.

$R_3$ is preferably a methyl radical or a perfluorinated methyl radical.

When $R_4$ is an alkyl group, having from 1 to 4 carbon atoms, substituted by at least one halogen atom, such as chlorine, bromine or fluorine, the halogen atom is preferably a fluorine atom.

$R_4$ is preferably a perhalogenated alkyl radical having from 1 to 4 carbon atoms and, more preferably still, $R_4$ is a perhalogenated methyl radical, preferably a perfluorinated methyl radical.

When R4 is an aryl group, it is preferably a phenyl radical. $R_3$ and $R_4$ preferably have a different meaning.

The compound used according to the invention is preferably chosen from N-(4-cyano-3-(trifluoromethyl)phenyl)-3,3,3-trifluoro-2-hydroxy-2-methylpropionamide, N-(3-chloro-4-cyanophenyl)-3,3,3-trifluoro-2-hydroxy-2-methylpropionamide, N-(3,4-dichlorophenyl)-3,3,3-trifluoro-2-hydroxy-2-methylpropionamide, N-(4-cyano-3-(trifluoromethyl)phenyl)-2-hydroxy-2-phenylpropionamide and N-(3,4-dicyanophenyl)-3,3,3-trifluoro-2-hydroxy-2-methylpropionamide.

These compounds can be used alone or as a mixture.

The effective amount of compound to be used corresponds, of course, to the amount necessary in order to obtain the desired result. A person skilled in the art is thus in a position to evaluate this effective amount, which depends on the nature of the compound used and on the person thus treated. To give an order of magnitude, according to the invention, in a cosmetic composition, the compound can be present at a concentration of between $10^{-6}\%$ and 5%, by weight with respect to the total weight of the composition, and preferably of between $10^{-3}\%$ and 1%. In the preparation of a pharmaceutical composition, the compound can be used at a concentration of between $10^{-5}\%$ and 10%, by weight with respect to the total weight of the composition, and preferably of between $10^{-2}\%$ and 2%.

The pharmaceutical composition according to the invention can be administered parenterally, enterally or topically. The pharmaceutical composition is preferably administered topically The physiologically acceptable medium in which the active principle is used according to the invention can be anhydrous or aqueous. Anhydrous medium is understood to mean a solvent medium containing less than 1% of water. This medium can be composed of a solvent or of a mixture of solvents chosen more particularly from $C_2$–$C_4$ lower alcohols, such as ethyl alcohol, alkylene glycols, such as propylene glycol, and alkylene glycol or dialkylene glycol alkyl ethers, the alkyl or alkylene radicals of which comprise from 1 to 4 carbon atoms. Aqueous medium is understood to mean a medium consisting of water or a mixture of water and another physiologically acceptable solvent chosen in particular from the abovementioned organic solvents. In the latter case, these other solvents, when they are present, represent approximately 5 to 95% by weight of the composition.

It is possible for the physiologically acceptable medium to be able to comprise other adjuvants commonly used in the cosmetic or pharmaceutical field, such as surface-active agents, thickening or gelling agents, cosmetic agents, preservatives, or basifying or acidifying agents well known in the state of the art, and in amounts sufficient for the desired presentation form to be obtained, in particular the more or less thickened lotion form, the gel form, the emulsion form or the cream form. Use can optionally be made in a form pressurized in an aerosol or vaporized from a pump-action spray.

It is also possible to use, in combination with the active principle, compounds which further improve the activity with respect to hair regrowth and/or with respect to slowing down hair loss and which have already been described for this activity.

Mention may more particularly be made, among the latter compounds, without implied limitation, of:

nicotinic acid esters, including in particular tocopherol nicotinate, benzyl nicotinate and $C_1$–$C_6$ alkyl nicotinates, such as methyl or hexyl nicotinates;

pyrimidine derivatives, such as 2,4-diamino-6-piperidinopyrimidine 3-oxide or "Minoxidil" disclosed in Patents U.S. Pat. No. 4,139,619 and U.S. Pat. No. 4,596,812;

agents which promote hair regrowth, such as those disclosed by the Applicant Company in the European Patent Application published under the number 0,648,488;

antibacterial agents, such as macrolides, pyranosides and tetracyclines, and in particular erythromycin;

calcium antagonists, such as cinnarizine, diltiazem, nimodipine and nifedipine;

hormones, such as oestriol or analogues, or thyroxine and its salts;

steroidal anti-inflammatory agents, such as corticosteroids (for example, hydrocortisone);

antiandrogens, such as oxendolone, spironolactone, diethylstilbestrol and flutamide;

steroidal or non-steroidal 5-α-reductase inhibitors, such as finasteride;

potassium agonists, such as cromakalira and nicorandil.

Other compounds can also be added to the above list, namely, for example, diazoxide, spiroxasone, phospholipids, such as lecithin, linoleic and linolenic acids, salicylic acid and its derivatives disclosed in French Patent FR 2,581,542, such as salicylic acid derivatives carrying an alkanoyl group having from 2 to 12 carbon atoms at the 5 position of the benzene ring, hydroxycarboxylic or ketocarboxylic acids and their esters, lactones and their corresponding salts, anthralin, carotenoids, eicosatetrayenoic and eicosatryenoic acids or their esters and amides, vitamin D and its derivatives, or extracts of plant or bacterial origin.

It is also possible to envisage the composition comprising at least one compound as defined above being in liposomed form, as disclosed, in particular, in Patent Application WO 94/22468, filed on Oct. 13, 1994 by the company Anti Cancer Inc. Thus, the compound encapsulated in the liposomes can be delivered selectively to the hair follicle.

The cosmetic composition according to the invention is to be applied to the alopecic areas of the scalp and hair of an individual and is optionally left in contact for several hours and is optionally to be rinsed out. It is possible, for example, to apply the composition comprising an effective amount of at least one compound as defined above in the evening, to keep the composition in contact overnight and, optionally, to shampoo in the morning. These applications can be repeated daily for one or more months according to the individual.

Thus, another subject-matter of the present invention is a process for the cosmetic treatment of the hair and/or the scalp, characterized in that it consists in applying, to the hair and/or the scalp, a composition comprising an effective amount of at least one compound as defined above, in leaving this composition in contact with the hair and/or the scalp, and optionally in rinsing.

The treatment process exhibits the characteristics of a cosmetic process insofar as it allows the attractiveness of the hair to be improved while giving it greater strength and an improved appearance.

Examples will now be given by way of illustration which should not be understood as limiting in any way the scope of the invention.

Example 1

$IC_{50}$ of the Compounds Determined for their Effect on the Potassium Channels and on the Androgen Receptors The $IC_{50}$ corresponds to the concentration which decreases by 50% either an induced pharmacological mechanism, such as muscular contraction, or the attachment of a molecule to its membrane receptor.

In order to determine the $IC_{50}$ of the compounds for their effect on the potassium channels, they were tested according to the methods of Newgreen et al. (Br. J. Pharmacol., 1990, 100, 605–613), Bray et al. (Arch. Pharmacol., 1991, 344, 351–359) and wickerden et al. (Br. J. Pharmacol., 1991, 103, 1148–1152).

In order to determine the $IC_{50}$ of the compounds for their effect on the androgen receptors, they were tested according to the method of Schilling and Liao ("The Prostate", 1984, 5, 581–588).

The values are given in $\mu M$

The following compounds were tested:

A: N-(4-cyano-3-(trifluoromethyl)phenyl)-3,3,3-trifluoro-2-hydroxy-2-methylpropionamide, B: N-(3-chloro-4-cyanophenyl)-3,3,3-trifluoro-2-hydroxy-2-methylpropionamide, C: N-(3,4-dichlorophenyl)-3,3,3-trifluoro-2-hydroxy-2-methylpropionamide, D: N-(4-cyano-3-(trifluoromethyl)phenyl)-2-hydroxy-2-phenylpropionamide, E: N-(3,4-dicyanophenyl)-3,3,3-trifluoro-2-hydroxy-2-methylpropionamide, F: N-(4-nitro-3-(trifluoromethyl)phenyl)-3,3,3-trifluoro-2-hydroxy-2-methylpropionamide;

G: N-(4-cyanophenyl)-3,3,3-trifluoro-2-hydroxy-2-methylpropionamide.

The compounds F and G, with structures similar to those of the compounds of the invention but not included within the definition of the compounds of the invention, were tested as comparatives.

| Compound | K⁺ Channels | Androgen receptors |
|---|---|---|
| A | 0.5 | 1 |
| B | 0.1 | 0.5 |
| C | 2 | 1 |
| D | 3 | 3 |
| E | 1 | 10 |
| F | >10 | >10 |
| G | 10 | >10 |

The molecules A, B, C, D and E exhibit a good affinity for the androgen receptor and an excellent opening effect for potassium channels, whereas, in comparison, the molecules F and G, similar in their structure but not coming within the scope of the invention, exhibit a poor affinity for the androgen receptor and a poor opening effect for potassium channels.

EXAMPLE 2

Examples of Compositions Containing an N-aryl-2-hydroxyalkylamide

These compositions are obtained by the usual techniques commonly used in cosmetics or in pharmaceuticals.

Lotion for Combating Hair Loss:

| | |
|---|---|
| N-(4-Cyano-3-(trifluoromethyl)phenyl)-3,3,3-trifluoro-2-hydroxy-2-methylpropionamide | 0.1 g |
| Propylene glycol | 10.0 g |
| Isopropyl alcohol | q.s. for 100.0 g |

1 ml of this lotion is applied to the scalp, at the rate of one to two times daily.

Niosomed Gel:

| | |
|---|---|
| Chimexane NS ® | 1.8 g |
| Monosodium stearoylglutamate | 0.2 g |
| N-(4-Cyano-3-(trifluoromethyl)phenyl)-2-hydroxy-2-phenylpropionamide | 1.0 g |
| Carbomer | 0.2 g |
| Triethanolamine | q.s. pH = 7 |
| Preservatives | q.s. |
| Fragrances | q.s. |
| Demineralized water | q.s. for 100.0 g |

This gel is applied to the scalp, one to two times daily.

Lotion for Combating Hair Loss:

| | |
|---|---|
| N-(3-Chloro-4-cyanophenyl)-3,3,3-trifluoro-2-hydroxy-2-methylpropionamide | 0.5 g |
| Propylene glycol | 30.0 g |
| Ethyl alcohol | 40.5 g |
| Water | q.s. for 100.0 g |

This lotion is applied to the scalp, one to two times daily, at the rate of 1 ml per application.

Thickened Lotion for Combating Hair Loss:

| | |
|---|---|
| N-(4-Cyano-3-(trifluoromethyl)phenyl)-3,3,3-trifluoro-2-hydroxy-2-methylpropionamide | 0.01 g |
| Kawaine | 2.0 g |
| Hydroxypropylcellulose, sold by the company Hercules under the name Klucel G | 3.5 g |
| Ethyl alcohol | q.s. for 100.0 g |

This thickened lotion is applied to the scalp, one to two times daily, at the rate of 1 ml per application.

Niosomed Lotion:

| | |
|---|---|
| Chimexane NL ® | 0.475 g |
| Cholesterol | 0.475 g |
| Monosodium stearoylglutamate | 0.05 g |
| N-(3,4-Dicyanophenyl)-3,3,3-trifluoro-2-hydroxy-2-methylpropionamide | 1.0 g |
| Preservatives | q.s. |
| Colorants | q.s. |
| Fragrance | q.s. |
| Demineralized water | q.s. for 100.0 g |

This lotion is applied to the scalp, one to two times daily, at the rate of 1 ml per application.

Lotion for Combating Hair Loss:

| | |
|---|---|
| N-(3,4-Dichlorophenyl)-3,3,3-trifluoro-2-hydroxy-2-methylpropionamide | 1.5 g |
| Propylene glycol monomethyl ether, sold under the name Dowanol PM by the company Dow Chemical | 20.0 g |
| Hydroxypropylcellulose, sold by the company Hercules under the name Klucel G | 3.0 g |
| Ethyl alcohol | 40.0 g |
| Water | q.s. for 100.0 g |

This thickened lotion is applied to the scalp, one to two times daily, at the rate of 1 ml per application.

With each of the compositions described in the above examples, a slower rate of hair loss and/or a regrowth effect was observed after several months of treatment and depending on the subjects treated.

What is claimed is:

1. A method for inducing and/or stimulating hair growth and/or slowing down hair loss in a human or animal in need of same, said method comprising applying to the hair and/or scalp of said human or animal, in an amount effective to induce and/or stimulate hair growth and/or to slow down hair loss, at least one compound having the formula (I):

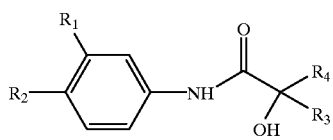

(I)

in which
- $R_1$ is a cyano group, a halogen atom or an alkyl group having from 1 to 4 carbon atoms, substituted by at least one halogen atom;
- $R_2$ is a cyano group;
- $R_3$ is an alkyl group having 1 or 2 carbon atoms, optionally substituted by at least one halogen atom;
- $R_4$ is a hydrogen atom or an alkyl group having from 1 to 4 carbon atoms, substituted by at least one halogen atom, or an aryl group, optionally substituted by one or more halogen atoms or by one or more hydroxyl, carboxyl, nitro, cyano, linear or branched alkyl having 1 to 4 carbon atoms, linear or branched alkoxy having 1 to 4 carbon atoms, linear or branched alkanoyl having 1 to 4 carbon atoms, or perfluoroalkyl groups; or at least one of its isomers, at least one of its acylated forms or at least one of its salts;

and optionally rinsing said compound from the hair and/or scalp.

2. The method according to claim 1, wherein $R_1$ is a chlorine, bromine or fluorine atom.

3. The method according to claim 2, wherein $R_1$ is a chlorine atom.

4. The method according to claim 1, wherein $R_1$ is an alkyl group having from 1 to 4 carbon atoms, substituted by at least one chlorine, bromine or fluorine atom.

5. The method according to claim 4, wherein $R_1$ is an alkyl group having from 1 to 4 carbon atoms, substituted by at least one fluorine atom.

6. The method according to claim 5, wherein $R_1$ is a perhalogenated alkyl radical having from 1 to 4 carbon atoms.

7. The method according to claim 6, wherein $R_1$ is a perhalogenated methyl radical.

8. The method according to claim 7, wherein $R_1$ is a perfluorinated methyl radical.

9. The method according to claim 1, wherein $R_3$ is a methyl radical or a perfluorinated methyl radical.

10. The method according to claim 1, wherein $R_4$ is an alkyl group having from 1 to 4 carbon atoms, substituted by at least one chlorine, bromine or fluorine atom.

11. The method according to claim 10, wherein $R_4$ is an alkyl group having from 1 to 4 carbon atoms, substituted by at least one fluorine atom.

12. The method according to claim 10, wherein the substituted alkyl group is a perhalogenated alkyl group.

13. The method according to claim 12, wherein the perhalogenated alkyl group is a perhalogenated methyl radical.

14. The method according to claim 1, wherein $R_4$ is a phenyl radical.

15. The method according to claim 1, wherein the compound of formula (I) is
- N-(4-cyano-3-(trifluoromethyl)phenyl)-3,3,3-trifluoro-2-hydroxy-2-methylpropionamide,
- N-(3-chloro 4-cyanophenyl)-3,3,3-trifluoro-2-hydroxy-2-methylpropionamide,
- N-(4-cyano-3-(trifluoromethyl)phenyl)-2-hydroxy-2-phenylpropionamide, or
- N-(3,4-dicyanophenyl)-3,3,3-trifluoro-2-hydroxy-2-methylpropionamide.

16. The method according to claim 1, wherein the compound of formula (I) is applied in the form of a cosmetic composition comprising said compound and a cosmetically acceptable carrier, said compound being present at a concentration of between $10^{-6}\%$ and 5%, by weight, with respect to the total weight of the composition.

17. The method according to claim 16, wherein said compound is present at a concentration of between $10^{-3}\%$ and 1%, by weight, with respect to the total weight of the composition.

18. The method according to claim 1, wherein the compound of formula (I) is applied in the form of a pharmaceutical composition comprising said compound and a pharmaceutically acceptable carrier, said compound being present at a concentration of between $10^{-5}\%$ and 10%, by weight, with respect to the total weight of the composition.

19. The method according to claim 18, wherein said compound is present at a concentration of between $10^{-2}\%$ and 2%, by weight, with respect to the total weight of the composition.

20. A topical cosmetic or pharmaceutical composition comprising, in an amount effective to induce and/or stimulate hair growth and/or to slow hair loss upon topical application to the scalp or hair, at least one compound having the formula (I):

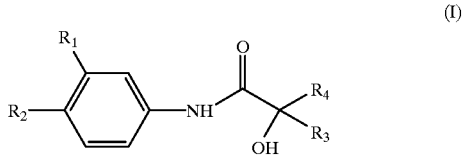

(I)

in which
- $R_1$ is a cyano group, a halogen atom or an alkyl group having from 1 to 4 carbon atoms, substituted by at least one halogen atom;

$R_2$ is a cyano group;

$R_3$ is an alkyl group having 1 or 2 carbon atoms, optionally substituted by at least one halogen atom;

$R_4$ is a hydrogen atom or an alkyl group having from 1 to 4 carbon atoms, substituted by at least one fluorine atom, or an aryl group, optionally substituted by one or more halogen atoms or by one or more hydroxyl, carboxyl, nitro, cyano, linear or branched alkyl having 1 to 4 carbon atoms, linear or branched alkoxy having 1 to 4 carbon atoms, linear or branched alkanoyl having 1 to 4 carbon atoms, or perfluoroalkyl groups; or at least one of its isomers, at least one of its acylated forms or at least one of its salts;

and a cosmetically or pharmaceutically acceptable topical carrier therefor; said composition being in the form of a topical lotion, gel, emulsion, cream or aerosol or pump-action spray.

21. The composition according to claim 20, wherein the compound of formula (I) is N-(4-cyano-3-(trifluoromethyl)phenyl)-3,3,3-trifluoro-2-hydroxy-2-methylpropionamide, N-(3-chloro-4-cyanophenyl)-3,3,3-trifluoro-2-hydroxy-2-methylpropionamide, N-(4-cyano-3-(trifluoromethyl)phenyl)-2-hydroxy-2-phenylpropionamide, or N-(3,4-dicyanophenyl)-3,3,3-trifluoro2-hydroxy-2-methylpropionamide.

22. A method for inducing and/or stimulating hair growth and/or slowing down hair loss in a human or animal in need of same, said method comprising applying to the hair and/or scalp of said human or animal, in an amount effective to induce and/or stimulate hair growth and/or to slow down hair loss, at least one compound having the formula (I):

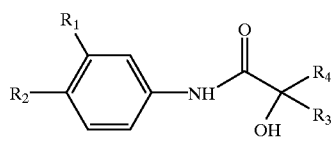

(I)

in which $R_1$ is a cyano group, a halogen atom or an alkyl group having from 1 to 4 carbon atoms, substituted by at least one halogen atom;

$R_2$ is a cyano group or a halogen atom;

$R_3$ is an alkyl group, having 1 or 2 carbon atoms, optionally substituted by at least one halogen atom;

$R_4$ is a perfluorinated methyl radical; or $R_4$ is an aryl group optionally substituted by one or more halogen atoms or by one or more hydroxyl, carboxyl, nitro, cyano, linear or branched alkyl having 1 to 4 carbon atoms, linear or branched alkoxy having 1 to 4 carbon atoms, linear or branched alkanoyl having 1 to 4 carbon atoms, or perfluoroalkyl groups; or at least one of its isomers, at least one of its acylated forms or at least one of its salts;

and optionally rinsing said compound from the hair and/or scalp.

23. The method according to claim 22, wherein $R_1$ is a chlorine, bromine or fluorine atom.

24. The method according to claim 23, wherein $R_1$ is a chlorine atom.

25. The method according to claim 22, wherein $R_1$ is an alkyl group having from 1 to 4 carbon atoms, substituted by at least one chlorine, bromine or fluorine atom.

26. The method according to claim 25, wherein $R_1$ is an alkyl group having from 1 to 4 carbon atoms, substituted by at least one fluorine atom.

27. The method according to claim 26, wherein $R_1$ is a perhalogenated alkyl radical having from 1 to 4 carbon atoms.

28. The method according to claim 27, wherein $R_1$ is a perhalogenated methyl radical.

29. The method according to claim 28, wherein $R_1$ is a perfluorinated methyl radical.

30. The method according to claim 22, wherein $R_2$ is a chlorine, bromine or fluorine atom.

31. The method according to claim 30, wherein $R_2$ is a chlorine atom.

32. The method according to claim 22, wherein $R_3$ is a methyl radical or a perfluorinated methyl radical.

33. The method according to claim 22, wherein $R_4$ is a perfluorinated methyl radical.

34. The method according to claim 22, wherein $R_4$ is a phenyl radical.

35. The method according to claim 22, wherein the compound of formula (I) is

N-(4-cyano-3-(trifluoromethyl)phenyl)-3,3,3-trifluoro-2-hydroxy-2-methylpropionamide, N-(3-chloro-4-cyanophenyl)-3,3,3-trifluoro-2-hydroxy-2-methylpropionamide, N-(3,4-dichlorophenyl)-3,3,3-trifluoro-2-hydroxy-2-methylpropionamide, N-(4-cyano-3-(trifluoromethyl)phenyl)-2-hydroxy-2-phenylpropionamide, or N-(3,4-dicyanophenyl)-3,3,3-trifluoro-2-hydroxy-2-methylpropionamide.

36. The method according to claim 22, wherein the compound of formula (I) is applied in the form of a cosmetic composition comprising said compound and a cosmetically acceptable carrier, said compound being present at a concentration of between $10^{-6}\%$ and 5%, by weight, with respect to the total weight of the composition.

37. The method according to claim 36, wherein said compound is present at a concentration of between $10^{-3}\%$ and 1%, by weight, with respect to the total weight of the composition.

38. The method according to claim 22, wherein the compound of formula (I) is applied in the form of a pharmaceutical composition comprising said compound and a pharmaceutically acceptable carrier, said compound being present at a concentration of between $10^{-5}\%$ and 10%, by weight, with respect to the total weight of the composition.

39. The method according to claim 38, wherein said compound is present at a concentration of between $10^{-2}\%$ and 2%, by weight, with respect to the total weight of the composition.

40. A topical cosmetic or pharmaceutical composition comprising, in an amount effective to induce and/or stimulate hair growth and/or to slow hair loss upon topical application to the scalp or hair, at least one compound having the formula (I):

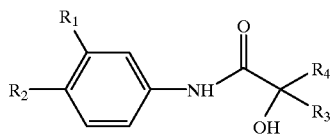 (I)

in which
- $R_1$ is a cyano group, a halogen atom or an alkyl group having from 1 to 4 carbon atoms, substituted by at least one halogen atom;
- $R_2$ is a cyano group or a halogen atom;
- $R_3$ is an alkyl group having 1 or 2 carbon atoms, optionally substituted by at least one halogen atom;
- $R_4$ is a perfluorinated methyl radical; or $R_4$ is an aryl group optionally substituted by one or more halogen atoms or by one or more hydroxyl, carboxyl, nitro, cyano, linear or branched alkyl having 1 to 4 carbon atoms, linear or branched alkoxy having 1 to 4 carbon atoms, linear or branched alkanoyl having 1 to 4 carbon atoms, or perfluoroalkyl groups; or at least one of its isomers, at least one of its acylated forms or at least one of its salts;

and a cosmetically or pharmaceutically acceptable topical carrier therefor; said composition being in the form of a topical lotion, gel, emulsion, cream or aerosol or pump-action spray.

41. The composition according to claim 40, wherein $R_4$ is a perfluorinated methyl radical.

42. The composition according to claim 41, wherein $R_4$ is a phenyl radical.

43. The composition according to claim 40, wherein the compound of formula (I) is N-(4-cyano-3-(trifluoromethyl)phenyl)-3,3,3-trifluoro-2-hydroxy-2-methylpropionamide, N-(3-chloro-4-cyanophenyl)-3,3,3-trifluoro-2-hydroxy-2-methylpropionamide, N-(3,4-dichlorophenyl)-3,3,3-trifluoro-2-hydroxy-2-methylpropionamide, N-(4-cyano-3-(trifluoromethyl)phenyl)-2-hydroxy-2-phenylpropionamide, or N-(3,4-dicyanophenyl)-3,3,3-trifluoro-2-hydroxy-2-methylpropionamide.

\* \* \* \* \*